US00PP23447P2

(12) United States Plant Patent
Booth et al.

(10) Patent No.: US PP23,447 P2
(45) Date of Patent: Mar. 5, 2013

(54) ***BEGONIA* PLANT NAMED 'BROTHGLOW'**

(50) Latin Name: ***Begonia* hybrid**
Varietal Denomination: BROTHGLOW

(76) Inventors: Caroline Booth, Congleton (GB); Claire Brown, Congleton (GB)

( * ) Notice: Subject to any disclaimer, the term of this patent is extended or adjusted under 35 U.S.C. 154(b) by 172 days.

(21) Appl. No.: 13/066,946

(22) Filed: Apr. 28, 2011

(51) Int. Cl.
*A01H 5/00* (2006.01)

(52) U.S. Cl. ..... Plt./343

(58) Field of Classification Search ..... Plt./343
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of tuberous *Begonia, Begonia* 'BROTHGLOW', characterized by its upright growth habit with good basal branching, its single male flowers that are apricot in color, and its evenly formed leaves that are dark olive green-bronze in color.

2 Drawing Sheets

Botanical classification: *Begonia* hybrid.
Cultivar designation: 'BROTHGLOW'.

RELATED APPLICATIONS

This application is related to an application filed for a cultivar derived from the same breeding program entitled *Begonia* Plant Named 'YABOS' (U.S. Plant Pat. No. 20,093).

BACKGROUND OF THE INVENTION

The present invention relates to a new and distinct cultivar of tuberous *Begonia* plant, botanically of hybrid origin and known as *Begonia* 'BROTHGLOW' and will be referred to hereafter by its cultivar name, 'BROTHGLOW'.

The new cultivar was derived from a controlled breeding program conducted by the inventors at a nursery in Congleton, Cheshire, U.K. The overall purpose of the breeding program is to make selections of *Begonia* plants with compact plant habits suitable for container use combined with superior flower performance and productive stock plants for propagation. 'BROTHGLOW' was selected as a whole plant mutation in May 2006 and derived from a cross made between 'YABOS' (U.S. Plant Pat. No. 20,093) as the female parent and an unnamed F1 hybrid from the Inventors' breeding program as the male parent.

Asexual reproduction of the new cultivar was first accomplished by terminal stem cuttings in Congleton, Cheshire, U.K. in 2006 by one of the Inventors. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'BROTHGLOW' as a new and distinct cultivar of *Begonia*.

1. 'BROTHGLOW' exhibits an upright growth habit.
2. 'BROTHGLOW' exhibits single male flowers that are apricot in color (female flowers are not produced).

3. 'BROTHGLOW' exhibits good basal branching and is particularly unique for its branching from small sized tubers.
4. 'BROTHGLOW' exhibits large evenly formed leaves that are dark olive green-bronze in color.

'BROTHGLOW' can readily be distinguished from its parents. 'YABOS', the female parent, differs from 'BROTHGLOW' in having a pendulous plant habit and in having flowers that are red-orange in color. The unnamed male parent differs from 'BROTHGLOW' in having flowers that are white in color. 'BROTHGLOW' is particularly unique for its combination of its single male only flowers that are apricot in color combined with it multi-branched upright habit and there are no cultivars of *Begonia* known to the Inventors that are close for comparison. 'BROTHGLOW' can be compared to existing cultivars of tuberous type *Begonias* with flowers that are apricot in color. The cultivars 'Apricot Delight' (not patented), Apricot Cascade' (not patented), and 'Innbellpea' (U.S. Plant Pat. No. 20,606) all differ from 'BROTHGLOW' in having pendulous plant habits and double flowers. 'Encanto Orange' (U.S. Plant Pat. No. 20,898) is similar to 'BROTHGLOW' in having single flowers, however the flowers of 'Encanto Orange' are bright orange in color and the plant habit is pendulous.

BRIEF DESCRIPTION OF THE DRAWING

The accompanying colored photographs illustrate the overall appearance and distinct characteristics of the new *Begonia*. The photographs were taken in August of a plant grown from a single, un-pinched plug in a 2-gallon container in Essex, United Kingdom.

The photograph in FIG. 1 provides a side view of 'BROTHGLOW' in bloom.

Figure 1:
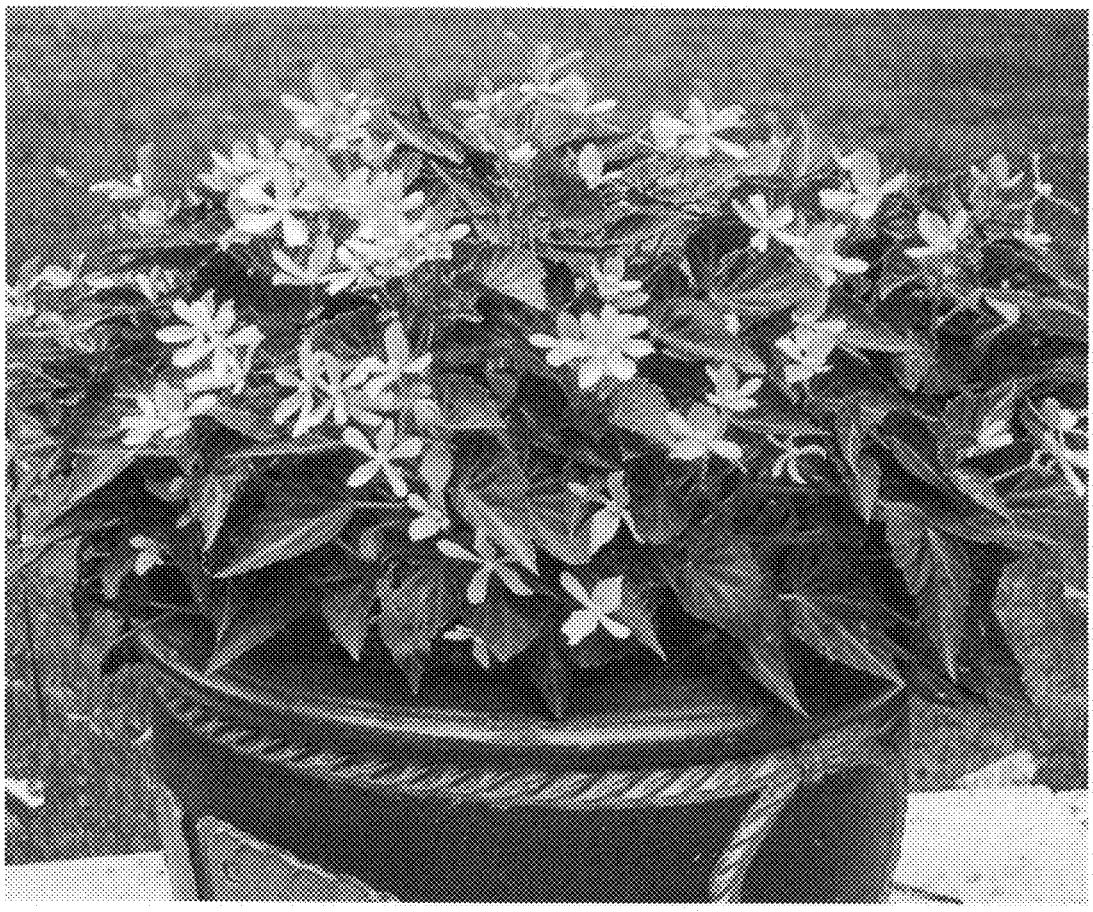
Figure 2:
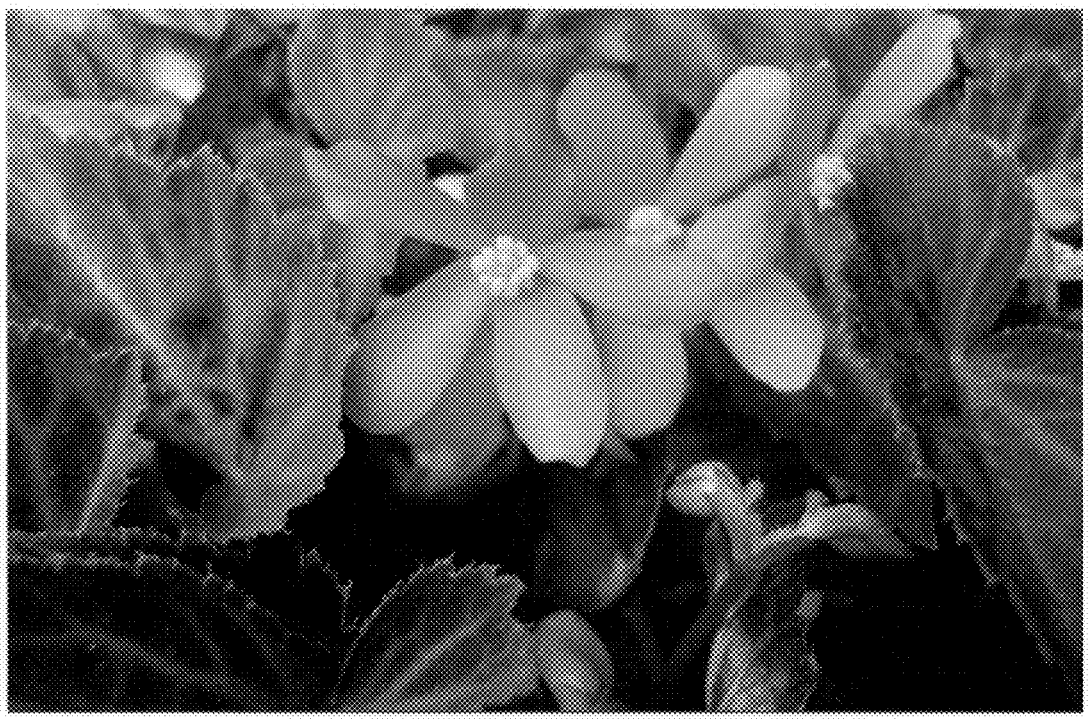

The photograph in FIG. 2 provides a close-up view of the flowers of 'BROTHGLOW'.

Figure 3:
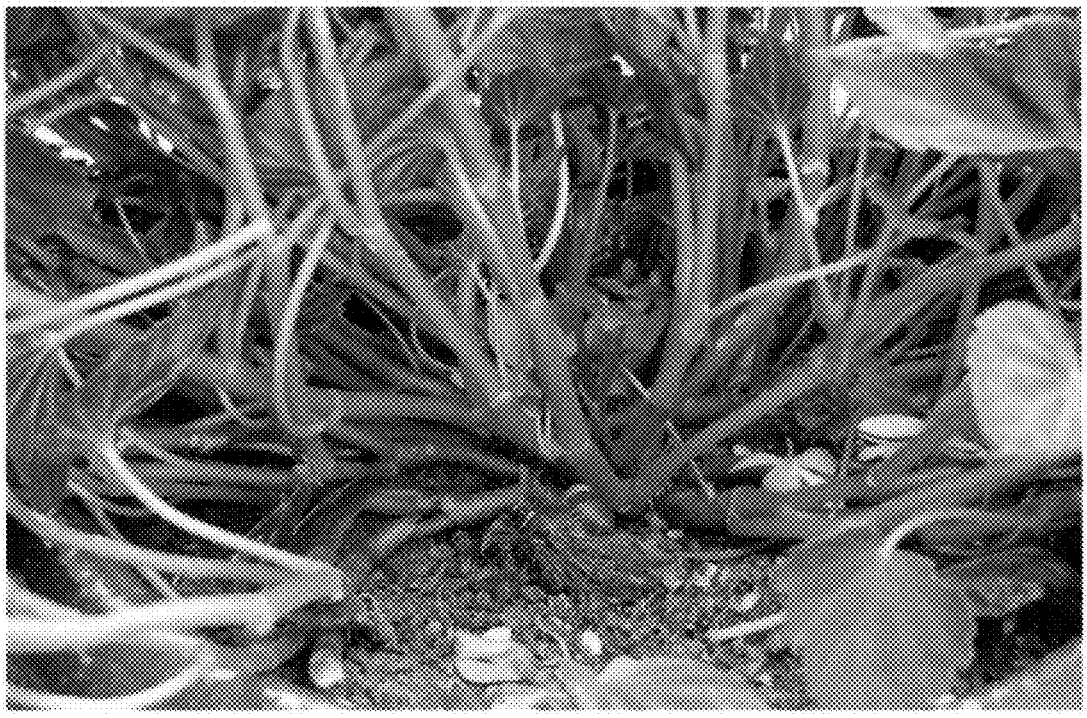

The photograph in FIG. 3 provides a close-up view of the basal branching.

The colors in the photograph may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately 2 months in age as grown in 4.5-inch containers under greenhouse conditions with ambient light in Congleton, Cheshire, U.K. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type.*—Deciduous tuberous perennial, grown primarily for use in patio pots, landscaping, bedding and containers.

*Plant habit.*—Upright, bushy, freely branched.

*Flowering period.*—From May to October.

*Height and spread.*—Reaches about 30 cm in height and about 20 cm in spread.

*Cold hardiness.*—USDA Zone 10.

*Culture.*—Good horticulture compost, 20° C. or more with a minimum of 12 hours of light needed for production in the winter months.

*Diseases and pests.*—No susceptibility or resistance to diseases or pests has been observed.

*Root description.*—Fleshy to fibrous with tubers produced for over-wintering.

*Tubers.*—Depressed in centre and irregularly lobbed in shape, average of 3.5 cm in length and 2 cm in width, smooth and slightly corky, color between 166D and N167D in color.

Growth and propagation:

*Growth rate.*—Very vigorous.

*Propagation.*—Stem tip cuttings.

*Time required for root initiation.*—10 to 14 days at 22° C.

*Time required for root development.*—5 to 8 weeks to reach commercial size.

Stem description:

*Stem size.*—Average of 20 cm in length and 6 mm in width with lateral branches about 4 mm in width.

*Stem shape.*—Round, solid.

*Stem color.*—174D.

*Stem surface.*—Pubescent with simple colorless hairs, lenticels absent.

*Internode length.*—Average of 15 mm.

*Branching habit.*—Freely branched.

*Branching angle at emergence.*—About 45°.

Foliage description:

*Leaf shape.*—Strongly asymmetric with one side narrow ovate, the other side narrow cordate.

*Leaf division.*—Entire.

*Leaf base.*—Weakly cordate.

*Leaf apex.*—Acuminate.

*Leaf venation.*—Pinnate, color 194B on upper surface and 195B on lower surface.

*Leaf margins.*—Irregular serrate with teeth tips drawn out into short bristles.

*Leaf attachment.*—Petiolate.

*Leaf arrangement.*—Alternate.

*Leaf surface.*—Upper surface; glabrous, velvety, lower surface; pubescent with short colorless simple hairs, glossy.

*Leaf color.*—Upper surface; a color between 200A and N186B; N137D along the veins, lower surface; 59A when young and maturing to 183A.

*Leaf size.*—Average of 7 cm in length and 4 cm in width.

*Leaf fragrance.*—None.

*Petioles.*—Ranges from 4 cm to 6 cm in length and 2 mm in width, surface is very sparsely pubescent with simple hairs, color is nearest 174D.

*Stipules.*—Triangular in shape, 194C in color and rapidly becoming dry and papery, about 4 mm in length and 3 mm width.

Flower description:

*Inflorescence type.*—2 to 3 single flowers produced in the axils of the upper leaves, terminal flower opens before the 2 lateral flowers, all flowers are male.

*Peduncles.*—About 7.5 cm in length and 2 mm in width, 179A in color, pubescence is absent.

*Flower persistence.*—Self-cleaning.

*Flower type.*—Single.

*Flower fragrance.*—None.

*Flower number.*—10 to 12 per branched stem.

*Flower aspect.*—Upright.

*Bracts.*—Typically 2, broad ovate in shape, obtuse apex, about 6 mm in length and 5 mm in width, 143C in color, margins 180B to 180C with stiff hairs.

Male flowers:

*Pedicels.*—About 11 to 21 mm in length and 1 mm in width, 179A in color, pubescence absent.

*Flower buds.*—Flattened ovoid in shape, about 19 mm in length and 12 mm in width, a blend of 180B and 47C in color, 146D at base.

*Flower shape.*—Open saucer-shaped.

*Flower size.*—About 2.1 cm in length and 5.1 cm in width.

*Outer tepal.*—2 in number, ovate in shape, obtuse apex, rounded base, average of 2.3 cm in length and 1.5 cm in width, glabrous and smooth on both inner and outer surfaces, entire margin, outer surface; 46D in color, inner surface; 32B in color.

*Inner tepal.*—2 to 3 in number, narrow ob-elliptic in shape, obtuse apex, narrow to cuneate base, average of 2.4 cm in length and 8 cm in width, glabrous and smooth on both inner and outer surfaces, entire margin, outer surface; 33D in color, inner surface; 30D in color.

*Corolla form.*—Spreading, tepals are un fused.

*Stamens.*—Connate below forming a tube, about 6 mm in length and 2 mm in width, 10A in color, numerous, approximately an average of 12 in number.

*Filaments.*—About 2 mm in length and 0.5 mm in width, 10D in color.

*Anthers.*—Ovoid in shape, about 1 mm in length and 1 mm in width, 10A in color.

*Pollen.*—Little to none in quantity, no obvious pollen present.

Female flowers: No female flowers formed.

Seed: No seeds produced.

It is claimed:

1. A new and distinct cultivar of *Begonia* plant named 'BROTHGLOW' as herein illustrated and described.

* * * * *